US008252821B2

(12) United States Patent
Chandran et al.

(10) Patent No.: US 8,252,821 B2
(45) Date of Patent: Aug. 28, 2012

(54) BIOAVAILABLE CAPSULE COMPOSITIONS OF AMORPHOUS ALPHA-(N-SULFONAMIDO)ACETAMIDE COMPOUND

(75) Inventors: Sachin Chandran, Highland Park, NJ (US); Rajesh Babulal Gandhi, Plainsboro, NJ (US); Jaquan Kalani Levons, Ewing, NJ (US); Robert Kevin Perrone, Belle Mead, NJ (US); Christopher P. Price, Kentfield, CA (US); Krishnaswamy Srinivas Raghavan, Cranbury, NJ (US); Ismat Ullah, Cranbury, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 212 days.

(21) Appl. No.: 12/758,385

(22) Filed: Apr. 12, 2010

(65) Prior Publication Data

US 2010/0260837 A1  Oct. 14, 2010

Related U.S. Application Data

(60) Provisional application No. 61/169,061, filed on Apr. 14, 2009.

(51) Int. Cl.
*A61K 31/4245* (2006.01)
*A61P 25/28* (2006.01)
(52) U.S. Cl. ..................................... 514/364
(58) Field of Classification Search ........................ None
See application file for complete search history.

(56) References Cited

U.S. PATENT DOCUMENTS

| 5,274,094 | A | 12/1993 | Whittaker et al. |
| 5,516,783 | A | 5/1996 | Whittaker et al. |
| 6,153,612 | A | 11/2000 | Ortwine et al. |
| 6,313,123 | B1 | 11/2001 | Levin et al. |
| 7,300,951 | B2 | 11/2007 | Kreft et al. |
| 7,687,666 | B2 | 3/2010 | Chan et al. |
| 7,786,122 | B2 | 8/2010 | Parker et al. |
| 7,838,550 | B2 | 11/2010 | Chan et al. |
| 8,084,477 | B2 * | 12/2011 | Starrett et al. ............... 514/364 |

FOREIGN PATENT DOCUMENTS

| JP | 11-343279 | 12/1999 |
| WO | WO 98/03166 | 1/1998 |
| WO | WO 00/44716 | 8/2000 |
| WO | WO 00/50391 | 8/2000 |
| WO | WO 03/053912 | 7/2003 |
| WO | WO 2005/042489 | 5/2005 |
| WO | WO 2005/095334 | 10/2005 |
| WO | WO 2006/005486 | 1/2006 |
| WO | WO 2006/034480 | 3/2006 |
| WO | WO 2007/098030 | 8/2007 |
| WO | WO 2008/112249 | 9/2008 |
| WO | WO 2009/005688 | 1/2009 |
| WO | WO 2009/058552 | 5/2009 |
| WO | WO 2009/137657 | 11/2009 |
| WO | WO 2010/107435 | 9/2010 |
| WO | WO 2010/107984 | 9/2010 |
| WO | WO 2010/107997 | 9/2010 |
| WO | WO 2010/108067 | 9/2010 |
| WO | WO 2010/120662 | 10/2010 |

OTHER PUBLICATIONS

U.S. Appl. No. 12/840,612, filed Jul. 21, 2010, Parker et al.
Chapman, P.F. et al., "Impaired synaptic plasticity and learning in aged amyloid precursor protein transgenic mice", Nature Neuroscience, vol. 2, No. 3, pp. 271-276 (1999).
Clarke, W.J. et al., "Gender Differences in Oral Drug Exposure in the Rat with the Gamma-Secretase Inhibitor BMS-708163", Drug Metab. Rev., Abstract No. 126, vol. 41, pp. 58-59 (2009).
Dahlgren, K.N. et al., "Oligomeric and Fibrillar Species of Amyloid-β Peptides Differentially Affect Neuronal Viability", The Journal of Biological Chemistry, vol. 277, No. 35, pp. 32046-32053 (2002).
Freebern, W.J. et al., "From Phenotyping to Host Resistance Models: A Comprehensive Immunotoxicologic Investigation of a Gamma Secretase Inhibitor in Rats", International Journal of Toxicology, Abstract No. P12, vol. 29, No. 1, pp. 91-92 (2010).
Gillman, K.W. et al., "Discovery and Evaluation of BMS-708163, a Potent, Selective and Orally Bioavailable γ-Secretase Inhibitor", ACS Medicinal Chemistry Letters, vol. 1, pp. 120-124 (2010).
Golde, T.E., "Alzheimer's disease therapy: Can the amyloid cascade be halted?", The Journal of Clinical Investigation, vol. 111, No. 1, pp. 11-18 (2003).
Götz, J. et al., "Formation of Neurofibrillary Tangles in P301L Tau Transgenic Mice Induced by Aβ42 Fibrils", Science, vol. 293, pp. 1491-1495 (2001).
Leil, T.A. et al. "Model-Based Trial Simulation for Optimal Collection of CSF Aβ Samples in Clinical Studies: Application for BMS-708163", Clin. Pharmacol. Ther., Abstract No. OII-B-2, vol. 87, Suppl. 1, p. S38 (2010).
Lewis, J. et al., "Enhanced Neurofibrillary Degeneration in Transgenic Mice Expressing Mutant Tau and APP", Science, vol. 293, pp. 1487-1491 (2001).
Loane, D.J. et al., "Amyloid precursor protein secretases as therapeutic targets for traumatic brain injury", Nature Medicine, Advance Online Publication, pp. 1-3 (Mar. 15, 2009).
Maharvi, G.M. et al., "A synthesis of the γ-secretase inhibitor BMS-708163", Tetrahedron Letters, online Oct. 14, 2010.
Mayer, S.C. et al., Discovery of Begacestat, a Notch-1-Sparing γ-Secretase Inhibitor for the Treatment of Alzheimer's Disease, Journal of Medicinal Chemistry, vol. 51, No. 23, pp. 7348-7351 (2008).
McLean, C.A. et al., "Soluble Pool of Aβ Amyloid as a Determinant of Severity of Neurodegeneration in Alzheimer's Disease", Annals of Neurology, vol. 46, No. 6, pp. 860-866 (1999).
Seiffert, D. et al., "Presenilin-1 and -2 are Molecular Targets for γ-Secretase Inhibitors", The Journal of Biological Chemistry, vol. 275, No. 44, pp. 34086-34091 (2000).

(Continued)

*Primary Examiner* — Kamal Saeed
(74) *Attorney, Agent, or Firm* — John F. Levis; Pamela A. Mingo

(57) ABSTRACT

Pharmaceutical capsule compositions containing the active compound (2R)-2-[[(4-chlorophenyl)sulfonyl][[2-fluoro-4-(1,2,4-oxadiazol-3-yl)phenyl]methyl]amino]-5,5,5-trifluoropentanamide, and polyethylene glycol (PEG), Vitamin E polyethylene glycol succinate, polyvinylpyrrolidone (PVP) or copovidone (PVP-Polyvinyl acetate), with or without citric acid, are provided.

30 Claims, No Drawings

OTHER PUBLICATIONS

Selkoe, D.J., "Alzheimer's Disease: Genes, Proteins, and Therapy", Physiological Reviews, vol. 81, No. 2, pp. 741-766 (2001).

Selkoe, D.J., "Cell Biology of the Amyloid β-Protein Precursor and the Mechanism of Alzheimer's Disease", Annu. Rev. Cell Biol., vol. 10, pp. 373-403 (1994).

Siemers, E.R. et al., "Effects of a γ-secretase inhibitor in a randomized study of patients with Alzheimer disease", Neurology, vol. 66, pp. 602-604 (2006).

Thal, D.R. et al., "Two Types of Sporadic Cerebral Amyloid Angiopathy", Journal of Neuropathology and Experimental Neurology, vol. 61, No. 3, pp. 282-293 (2002).

Walsh, D.M. et al., "Naturally secreted oligomers of amyloid β protein potently inhibit hippocampal long-term potentiation in vivo", Nature, vol. 416, pp. 535-539 (2002).

Watkins, T.A. et al., "Distinct Stages of Myelination Regulated by γ-Secretase and Astrocytes in a Rapidly Myelinating CNS Coculture System", Neuron, vol. 60, pp. 555-569 (2008).

Wolfe, M.S., "Secretase Targets for Alzheimer's Disease: Identification and Therapeutic Potential", Journal of Medicinal Chemistry, vol. 44, No. 13, pp. 2039-2060 (2001).

Zhang D. et al., "Disposition of a Gamma-Secretase Inhibitor 14C-Labeled BMS-708163 in Mice, Rats, Rabbits, Dogs, and Humans. Applications of Bile Collection in Differentiating Oxidative Versus Reductive Metabolic Pathways", Drug Metab. Rev., Abstract No. 127, vol. 41, pp. 59-60 (2009).

2008 CSHL Meeting on Neurodegenerative Diseases, Oral Presentation: "BMS-708163, a Potent and Selective Gamma-Secretase Inhibitor, Decreases CSF A-Beta at Safe and Tolerable Doses in Animals and Humans", Dec. 5, 2008.

2009 BMS URG Symposium, Oral Presentation: "The Discovery of BMS-708163: a Potent and Selective Gamma-Secretase Inhibitor for the Treatment of Alzheimer's Disease", May 1, 2009.

237th National American Chemical Society Meeting, Salt Lake City, UT, Oral Presentation: "The Discovery of BMS-708163: A Potent and Selective Gamma-Secretase Inhibitor Which Lowers CSF Beta-Amyloid in Humans", Mar. 22, 2009.

Alzheimer's Association International Conference on Alzheimer's Disease, Chicago, IL, Abstract, Jul. 26, 2008.

Alzheimer's Association International Conference on Alzheimer's Disease, Chicago, IL, Oral Presentation: "BMS-708163, A Potent and Selective Gamma-Secretase Inhibitor, Decreases CSF A-Beta at Safe and Tolerable Doses in Animals and Humans", Jul. 30, 2008.

Alzheimer's Association International Conference on Alzheimer's Disease, Honolulu, HI, Poster: "A Comprehensive Immunotoxicologic Investigation of a Gamma Secretase Inhibitor in Rats", Jul. 10-15, 2010.

Alzheimer's Association International Conference on Alzheimer's Disease, Honolulu, HI, Poster: "A Placebo-Controlled Ascending Multiple-Dose Study to Evaluate the Safety, Pharmacokinetics, and Pharmacodynamics of BMS-708163 in Healthy Young and Elderly Subjects", Jul. 10-15, 2010.

Alzheimer's Association International Conference on Alzheimer's Disease, Honolulu, HI, Poster: "Study to Evaluate the Effects of Single Oral Doses of BMS-708163 on the Cerebrospinal Fluid A-Beta Level in Healthy Young Men", Jul. 10-15, 2010.

Alzheimer's Association International Conference on Alzheimer's Disease, Honolulu, HI, Poster: "Effect of Concomitant Administration of Multiple Doses of BMS-708163 on Safety and Tolerability and the Pharmacokinetics of Midazolam, Warfarin, Caffeine, Omeprazole, and Dextromethorphan in Healthy Male Subjects by Administration of a Modified Cooperstown Cocktail", Jul. 10-15, 2010.

Alzheimer's Association International Conference on Alzheimer's Disease, Honolulu, HI, Poster: "Gamma-Secretase Inhibitors Have Intrinsically Different Inhibitory Potencies Against A-Beta Production and Notch Signaling", Jul. 10-15, 2010.

Alzheimer's Association International Conference on Alzheimer's Disease, Honolulu, HI, Poster: "Separation of A-Beta Reduction from Notch Toxicity with Gamma-Secretase Inhibitors in Rats", Jul. 10-15, 2010.

Alzheimer's Association International Conference on Alzheimer's Disease, Honolulu, HI, Poster: "The Safety, Tolerability, Pharmacokinetics, and Pharmacodynamics of Single and Multiple Doses of BMS-708163 in Young and Elderly Japanese Subjects", Jul. 10-15, 2010.

Alzheimer's Association International Conference on Alzheimer's Disease, Honolulu, HI, Poster: "The Safety, Tolerability, Pharmacokinetics, and Pharmacodynamics of Single Doses of BMS-708163 in Young and Elderly Subjects", Jul. 10-15, 2010.

American Association of Pharmaceutical Sciences, New Orleans, LA, Oral Presentation: "Simple Allometric Scaling Predicts the Human Dose of BMS-708163, a Gamma Secretase Inhibitor Intended for the Treatment of Alzheimer's Disease", Nov. 14-18, 2010.

AMRI 2010 Integrated Drug Discovery Symposium, Oral Presentation: "Selection and Optimization of a Series of Gamma-Secretase Inhibitors: The Discovery of BMS-708163", Oct. 12-14, 2010.

Bristol-Myers Squibb Symposium, University of California, Irvine, CA, Oral Presentation: "Testing the Amyloid Hypothesis: The Discovery of Brain Penetrant Gamma-Secretase Inhibitors for the Treatment of Alzheimer's Disease", Jun. 2, 2010.

Gordon Research Conference, Newport, RI, Oral Presentation: "Heterocyclic Gamma-Secretase Inhibitors for the Treatment of Alzheimer's Disease", Jun. 30, 2009.

International Society for the Study of Xenobiotics Meeting, Baltimore, MD, Poster: "Gender Differences in Oral Drug Exposure of the Gamma Secretase Inhibitor, BMS-708163, in the Rat", Oct. 18-22, 2009.

Presentation to Department of Chemistry at the University of Arkansas, Fayetteville, AK, Oral Presentation: "Neuroscience Drug Discovery at Bristol-Myers Squibb", Apr. 15, 2010.

* cited by examiner

BIOAVAILABLE CAPSULE COMPOSITIONS OF AMORPHOUS ALPHA-(N-SULFONAMIDO)ACETAMIDE COMPOUND

CROSS-REFERENCE TO RELATED APPLICATIONS

This application claims the benefit of U.S. Provisional Application Ser. No. 61/169,061 filed Apr. 14, 2009.

FIELD OF THE INVENTION

The present invention relates to pharmaceutical formulations containing the Beta amyloid peptide production inhibitor compound (2R)-2-[[(4-chlorophenyl)sulfonyl][[2-fluoro-4-(1,2,4-oxadiazol-3-yl)phenyl]methyl]amino]-5,5,5-trifluoropentanamide, and more particularly, to pharmaceutical capsule compositions containing (2R)-2-[[(4-chlorophenyl)sulfonyl][[2-fluoro-4-(1,2,4-oxadiazol-3-yl)phenyl]methyl]amino]-5,5,5-trifluoropentanamide together with one or more pharmaceutically acceptable polymers that are storage stable for extended periods and are orally bioavailable with good in vivo absorption.

BACKGROUND OF THE INVENTION

Alzheimer's disease (AD) is a progressive neurodegenerative disease which begins with memory loss and progresses to include severe cognitive impairment, altered behavior, and decreased motor function (Grundman, M. et al., *Arch Neurol.*, 61:59-66 (2004); Walsh, D. M. et al., *Neuron*, 44:181-193 (2004)). It is the most common form of dementia and represents the third leading cause of death after cardiovascular disorders and cancer. The cost of AD is enormous and includes the suffering of the patients and families and the lost productivity of patients and caregivers. No treatment that effectively prevents AD or reverses the clinical symptoms and underlying pathophysiology is currently available.

A definitive diagnosis of AD for a demented patient requires a histopathological evaluation of the number and localization of neuritic plaques and neurofibrillary tangles upon autopsy (Consensus recommendations for the postmortem diagnosis of Alzheimer's disease. *Neurobiol. Aging*, 18:S1-S2 (1997)). Similar alterations are observed in patients with Trisomy 21 (Down syndrome). Plaques primarily consist of β-amyloid (Aβ) peptide that are formed by a stepwise proteolytic cleavage of the amyloid precursor protein (APP) by β-site APP-cleaving enzyme (BACE), to generate the N-terminus, and γ-secretase, to generate the C-terminus (Selkoe, D. J., *Physiol. Rev.*, 81:741-766 (2001)). γ-Secretase is a transmembrane protein complex that includes Nicastrin, Aph-1, PEN-2, and either Presenilin-1 (PS-1) or Presenilin-2 (PS-2) (Wolfe, M. S. et al., *Science*, 305.1119-1123 (2004)). PS-1 and PS-2 are believed to contain the catalytic sites of γ-secretase.

Aβ40 is the most abundant form of Aβ synthesized (80-90%), while Aβ42 is most closely linked with AD pathogenesis. In particular, mutations in the APP, PS-1, and PS-2 genes that lead to rare, familial forms of AD implicate Aβ42 aggregates as the primary toxic species (Selkoe, D. J., *Physiol. Rev.*, 81:741-766 (2001)). Current evidence suggests that oligomerie, protofibrillar and intracellular Aβ42 play a significant role in the disease process (Cleary, J. P. et al., *Nat. Neurosci.*, 8:79-84 (2005)). Inhibitors of the enzymes that form Aβ42, such as γ-secretase, represent potential disease-modifying therapeutics for the treatment of AD.

γ-Secretase cleaves multiple type I transmembrane proteins in addition to APP (Pollack, S. J. et al., *Curr. Opin. Investig. Drugs*, 6:35-47 (2005)). While the physiological significance of most of these cleavage events is unknown, genetic evidence indicates that γ-secretase cleavage of Notch is required for Notch signaling (Artavanis-Tsakonas, S. et al., *Science*, 284(5415):770-776 (1999); Kadesch, T., *Exp. Cell Res.*, 260(1):1-8 (2000)). In rodents dosed with γ-secretase inhibitors, drug-related toxicity has been identified in the gastrointestinal (GI) tract, thymus, and spleen (Searfoss, G. H. et al., *J. Biol. Chem.*, 278:46107-46116 (2003); Wong, G. T. et al., *J. Biol. Chem.*, 279:12876-12882 (2004); Milano, J. et al., *Toxicol. Sci.*, 82:341-358 (2004)). These toxicities are likely linked to inhibition of Notch signaling (Jensen, J. et al., *Nat. Genet.*, 24:36-44 (2000)).

The identification of mechanism-based toxicity raises the question of whether an acceptable therapeutic index can be achieved with γ-secretase inhibitors. Selective inhibition of Aβ formation over Notch processing, pharmacokinetics, drug disposition and/or tissue-specific pharmacodynamics could impact therapeutic margin.

Evidence suggests that a reduction in brain Aβ levels by inhibition of γ-secretase may prevent the onset and progression of AD (Selkoe, D. *Physiol. Rev.*, 81:741-766 (2001); Wolfe, M., *J. Med. Chem.*, 44:2039-2060 (2001)). There are emerging data for the role of Aβ in other diseases, including mild cognitive impairment (MCI), Down syndrome, cerebral amyloid angiopathy (CAA), dementia with Lewy bodies (DLB), amyotrophic lateral sclerosis (ALS-D), inclusion body myositis (IBM), and age-related macular degeneration. Advantageously, compounds that inhibit γ-secretase and reduce production of Aβ could be used to treat these or other Aβ-dependent diseases.

Excess production and/or reduced clearance of Aβ causes CAA (Thal, D. et al., *J. Neuropath. Exp. Neuro.*, 61:282-293 (2001)). In these patients, vascular amyloid deposits cause degeneration of vessel walls and aneurysms that may be responsible for 10-15% of hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients. Compounds that specifically target γ-secretase could reduce or prevent CAA.

DLB manifests with visual hallucinations, delusions, and parkinsonism. Interestingly, familial AD mutations that cause Aβ deposits can also cause Lewy bodies and DLB symptoms (Yokota, O. et al., *Acta Neuropathol.* (*Berl.*), 104:637-648 (2002)). Further, sporadic DLB patients have Aβ deposits similar to those in AD (Deramecourt, V. et al., *J. Neuropathol. Exp. Neurol.*, 65:278-288 (2006)). Based on this data, Aβ likely drives Lewy body pathology in DLB and, therefore, γ-secretase inhibitors could reduce or prevent DLB.

Approximately 25% of ALS patients have significant dementia or aphasia (Hamilton, R. L. et al., *Acta Neuropathol.* (*Berl.*), 107:515-522 (2004)). The majority (~60%) of these patients, designated ALS-D, contain ubiquitin-positive inclusions comprised primarily of the TDP-43 protein (Neumann, M. et al., *Science*, 314:130-133 (2006)). About 30% of the ALS-D patients have amyloid plaques consistent with Aβ causing their dementia (Hamilton, R. L. et al., *Acta Neuropathol.* (*Berl.*), 107:515-522 (2004)). These patients should be identifiable with amyloid imaging agents and potentially treatable with γ-secretase inhibitors.

IBM is a rare, age-related degenerative disease of skeletal muscle. The appearance of Aβ deposits in IBM muscle and the recapitulation of several aspects of the disease by directing APP overexpression to muscle in transgenic mice support the role of Aβ in IBM (reviewed in Murphy, M. P. et al., *Neurology*, 66:S65-S68 (2006)). Compounds that specifically target γ-secretase could reduce or prevent IBM.

In age-related macular degeneration, Aβ was identified as one of several components of drusen, extracellular deposits beneath the retinal pigment epithelium (RPE) (Anderson, D. H. et al., *Exp. Eye Res.*, 78:243-256 (2004)). A recent study has shown potential links between Aβ and macular degeneration in mice (Yoshida, T. et al., *J. Clin. Invest.*, 115:2793-2800 (2005)). Increases in Aβ deposition and supranuclear cataracts have been found in AD patients (Goldstein, L. E. et al., *Lancet*, 361:1258-1265 (2003)). Compounds that specifically target γ-secretase could reduce or prevent age-related macular degeneration.

Based on the role of Notch signaling in tumorigenesis, compounds which inhibit γ-secretase may also be useful as therapeutic agents for the treatment of cancer (Shih, I.-M., et al., *Cancer Res.*, 67:1879-1882 (2007)).

Compounds which inhibit gamma secretase may also be useful in treating conditions associated with loss of myelination, for example multiple sclerosis (Watkins, T. A. et al., *Neuron*, 60:555-569 (2008)).

A recent study by Georgetown University Medical Center researchers suggests that gamma-secretase inhibitors may prevent long-term damage from traumatic brain injury (Loane, D. J. et al., *Nat. Med.*, 1-3 (2009)).

Smith, et al. in International Application No. WO 00/50391, published Aug. 31, 2000, disclose a series of sulfonamide compounds that can act to modulate production of amyloid β protein as a means of treating a variety of diseases, especially Alzheimer's disease and other diseases relating to the deposition of amyloid.

Japanese Patent No. 11343279, published Dec. 14, 1999 discloses a series of sulfonamide derivatives which are TNF-alpha inhibitors useful for treating autoimmune diseases.

Parker et al. in International Application No. WO 03/053912, published Jul. 3, 2003, disclose a series of α-(N-sulphonamido)acetamide derivatives as β-amyloid inhibitors which are useful for the treatment of Alzheimer's disease and other conditions associated with β-amyloid peptide.

It has now been further discovered that an α-(N-sulphonamido)acetamide compound known as (2R)-2-[[(4-chlorophenyl)sulfonyl][[2-fluoro-4-(1,2,4-oxadiazol-3-yl)phenyl]methyl]amino]-5,5,5-trifluoropentanamide possesses unique attributes which make it useful for the treatment of Alzheimer's disease and other conditions associated with β-amyloid peptide. This compound is set forth and described in co-pending application with U.S. patent application Ser. No. 12/249,180, filed Oct. 10, 2008, the contents of which are incorporated herein in their entirety.

Unfortunately, (2R)-2-[[(4-chlorophenyl)sulfonyl][[2-fluoro-4-(1,2,4-oxadiazol-3-yl)phenyl]methyl]amino]-5,5,5-trifluoropentanamide has poor aqueous solubility that is often characterized as <1 ug/mL at about room temperature. Moreover, there has been shown no appreciable improvement in bioavailability by particle size reduction. In addition, solid dosage forms containing the drug compound in a crystalline form showed low oral bioavailability in dogs. Thus, it now appears that in order to provide optimal exposure of the API, a solid dosage form containing the active compound in a non-crystalline form should be provided.

What is therefore now needed in the art is one or more capsule formulations containing the active compound (2R)-2-[[(4-chlorophenyl)sulfonyl][[2-fluoro-4-(1,2,4-oxadiazol-3-yl)phenyl]methyl]amino]-5,5,5-trifluoropentanamide, including pharmaceutically acceptable salts thereof, together with one or more pharmaceutically acceptable polymers. These formulations should preferably display enhanced bioavailability and reduced degradation properties.

SUMMARY OF THE INVENTION

In one embodiment, the present invention provides a pharmaceutical composition comprising (2R)-2-[[(4-chlorophenyl)sulfonyl][[2-fluoro-4-(1,2,4-oxadiazol-3-yl)phenyl]methyl]amino]-5,5,5-trifluoropentanamide, polyethylene glycol (PEG), Vitamin E polyethylene glycol succinate, one crystallization inhibitor member selected from the group consisting of polyvinylpryrrolidone (PVP) and copovidone (PVP-Polyvinyl acetate), and citric acid.

In a further embodiment, there is provided a pharmaceutical capsule containing the above composition. This pharmaceutical capsule is preferably a hard gel capsule.

Also provided herein is a method of making a pharmaceutical composition which comprises dissolving (2R)-2-[[(4-chlorophenyl)sulfonyl][[2-fluoro-4-(1,2,4-oxadiazol-3-yl)phenyl]methyl]amino]-5,5,5-trifluoropentanamide in a mixture of PEG, Vitamin E PEG succinate, a crystallization inhibitor member, and citric acid. In a further step, the resultant mixture is put into a pharmaceutical capsule.

In another embodiment of the invention, there is provided a pharmaceutical composition comprising (2R)-2-[[(4-chlorophenyl)sulfonyl][[2-fluoro-4-(1,2,4-oxadiazol-3-yl)phenyl]methyl]amino]-5,5,5-trifluoropentanamide, polyethylene glycol (PEG), Vitamin E polyethylene glycol succinate, one crystallization inhibitor member selected from the group consisting of polyvinylpryrrolidone (PVP) and copovidone (PVP-Polyvinyl acetate), and no citric acid. For this embodiment, there is also provided a pharmaceutical capsule containing the aforesaid composition. This pharmaceutical capsule is preferably a soft gel capsule.

Also provided herein is a method of making a pharmaceutical composition which comprises dissolving (2R)-2-[[(4-chlorophenyl)sulfonyl][[2-fluoro-4-(1,2,4-oxadiazol-3-yl)phenyl]methyl]amino]-5,5,5-trifluoropentanamide in a mixture of PEG, Vitamin E PEG succinate, a crystallization inhibitor member, and no citric acid. In a further step, the resultant mixture is put into a pharmaceutical capsule.

In a further embodiment of the invention there is provided a method of treating or delaying the onset of Alzheimer's disease, cerebral amyloid angiopathy, mild cognitive impairment and/or Down syndrome, as well as the treatment of head trauma, traumatic brain injury, and/or dementia pugilistica, which comprises administering to a patient a therapeutically effective amount of a pharmaceutical capsule composition according to one or more of the embodiments herein described.

The present invention is directed to these, as well as other important ends, hereinafter described.

DETAILED DESCRIPTION OF THE INVENTION (2R)-2-[[(4-chlorophenyl)sulfonyl][[2-fluoro-4-(1,2,4-oxadiazol-3-yl)phenyl]methyl]amino]-5,5,5-trifluoropentanamide having the Formula I, including its pharmaceutically acceptable salts thereof, has now been found useful in inhibiting Aβ production in patients suffering from or susceptible to Alzheimer's disease (AD) or other disorders associated with β-amyloid peptide.

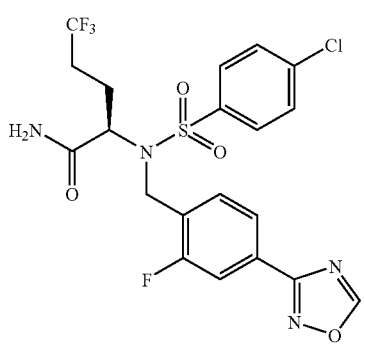

This compound has the chemical formula $C_{20}H_{17}ClF_4N_4O_4S$, and a molecular weight of 520.88.

According to a first embodiment, there is provided a composition comprising about 0.1 to 20% of the active compound (2R)-2-[[(4-chlorophenyl)sulfonyl][[2-fluoro-4-(1,2,4-oxadiazol-3-yl)phenyl]methyl]amino]-5,5,5-trifluoropentanamide, together with up to about 90% of polyethylene glycol (PEG) as solubilizer, and up to about 90% of Vitamin E polyethylene glycol succinate (TPGS) as co-solubilizer/surfactant, about 0.1 to 20% of a crystallization inhibitor member selected from the group consisting of polyvinylpryrrolidone (PVP) and copovidone (PVP-Polyvinyl acetate), and about 0.05 to 5% of citric acid as a stabilizer. (Unless otherwise stated, percentage (%) of components is provided on a weight/weight or "w/w" basis). Preferably, there is provided a composition containing about 0.1 to 20% of the active compound, together with about 35 to 90% of PEG, about 2 to 60% of TPGS, about 0.1 to 20% of the crystallization inhibitor member, and about 0.05 to 5% of citric acid. Even more preferably, there is provided a composition containing about 0.1 to 10% of the active compound, together with about 50 to 85% of PEG, about 5 to 40% of TPGS, about 1 to 10% of the crystallization inhibitor member, and about 0.05 to 1% of citric acid. These compositions are especially well adapted for use with hard gel capsules, hereinafter described.

It is preferred that the polyethylene glycol (PEG) component be PEG 1450. PEG 1450 has demonstrated enhanced solubilization of the active compound. It is preferred over such compounds as PEG 3550, PEG 4000 and PEG 6000, etc. The active compound (2R)-2-[[(4-chlorophenyl)sulfonyl][[2-fluoro-4-(1,2,4-oxadiazol-3-yl)phenyl]methyl]amino]-5,5,5-trifluoropentanamide has shown to have about 25 to 30% higher solubility in PEG 1450, as compared to PEG 3350 at about 60° C.

As stated above, Vitamin E Polyethylene Glycol Succinate (TPGS) is the preferred co-solubilizer/surfactant for the active compound. In certain embodiments, the TPGS can also be present as the sole solubilizer/surfactant in the composition of the invention. Formulations containing TPGS have now been shown to provide superior resistance to precipitation of the water-insoluble active compound following aqueous dilution, compared to formulations containing other surfactants such as the polyoxyethylene sorbitan monooleates (Polysorbates, e.g., Polysorbate 80). This property provides for increased oral absorption since the drug is not well absorbed orally from a crystalline state. In addition, as shown in Table IV hereinbelow, stability studies indicated formulations containing TPGS demonstrated superior stability (i.e., lower levels of the degradant compound formed from the active) as compared to counterpart formulations containing other surfactants such as the polyoxyethylene sorbitan monooleates (Polysorbates, e.g., Polysorbate 80) and the polyoxyethylene-polyoxypropylene glycol block copolymers (for example Polaxamer 407 or PLURONIC® F127).

The crystallization inhibitor member component of the composition is one member selected from the group consisting of polyvinylpryrrolidone (PVP) and copovidone (PVP-Polyvinyl acetate). It is preferred that the crystallization inhibitor by either PVP or PVP-Polyvinyl acetate. The water soluble polyvinylpyrrolidone (povidone) polymers and polyvinlyprrolidone-polyvinylacetate (copovidone) copolymers provide additional resistance to crystallization of the active drug compound during storage of the dosage forms and following aqueous dilution. The average molecular weight of polyvinylpyrrolidones (povidones) used in the present formulations may be in the range of from about 2,000 to about 54,000, but preferably in the range from about 2,000 to about 30,000, to help ensure that a liquid fill is obtained. Preferred polyvinylpyrrolidones are sold under trademarks KOLLIDON® 12 PF, KOLLIDON® 17 PF, KOLLIDON® 25 and KOLLIDON® 30 by BASF Corporation. The preferred average molecular weight of polyvinlyprrolidone-polyvinylacetate (copovidones) used in the formulations of the invention may be in the range of about 45,000 to 70,000, to help ensure that a liquid fill is obtained. The preferred polyvinlyprrolidone-polyvinylacetate (copovidone) is sold under the trademark KOLLIDON® VA64 by BASF Corporation. Alternative or additional crystallization inhibitor members that may be included in the formulations include the water-soluble cellulose ether derivatives (for example: hydroxypropylcellulose, hydroxypropylmethylcellulose) and the like.

As stated, citric acid is the preferred stabilizer that may be included in the formulation. Other pharmaceutically acceptable stabilizers of the active compound include various inorganic acids (for example: hydrochloric acid, and the like) or other organic mono-, di-, or tri-carboxylic acids (for example: acetic acid, ascorbic acid, methanesulfonic acid, succinic acid, tartaric acid, and the like) and various salts of these acids (for example sodium citrate, sodium succinate, sodium tartrate, and the like).

Other excipients such as pharmaceutical-grade fillers and binders available in the art may also be incorporated therein the composition, but this is optional. The formulations may optionally also contain a pharmaceutically acceptable antioxidant for stabilization of the dosage form. Examples include ascorbic acid, BHA, BHT, propyl gallate, Vitamin E, and the like.

In order to prepare the compositions hereinabove described, various preparation means available to the skilled artisan may be utilized. It is preferred that the compound (2R)-2-[[(4-chlorophenyl)sulfonyl][[2-fluoro-4-(1,2,4-oxadiazol-3-yl)phenyl]methyl]amino]-5,5,5-trifluoropentanamide be dissolved at elevated temperature in an admixture solution of the polyethylene glycol (PEG), Vitamin E polyethylene glycol succinate, crystallization inhibitor member, and citric acid using apparatus and procedures available in the art.

In a further embodiment of the invention, there is provided another composition of the invention. According to this embodiment, there is provided 0.1 to 25% of the active compound (2R)-2-[[(4-chlorophenyl)sulfonyl][[2-fluoro-4-(1,2,4-oxadiazol-3-yl)phenyl]methyl]amino]-5,5,5-trifluoropentanamide, together with up to about 90% of polyethylene glycol (PEG) as solubilizer, and up to about 90% of Vitamin E polyethylene glycol succinate (TPGS) as co-solubilizer/surfactant, about 0.1 to 20% of a crystallization inhibitor member selected from the group consisting of polyvinylpryrolidone (PVP) and copovidone (PVP-Polyvinyl acetate), and no citric acid stabilizer. Preferably, there is provided a composition containing about 0.1 to 20% of the active compound, together with about 5 to 75% of PEG, about 5 to 75% of TPGS, about 0.1 to 20% of the crystallization inhibitor member, and no citric acid stabilizer. Even more preferably, there is provided a composition containing about 0.5 to 20% of the active compound, together with about 10 to 30% of PEG, about 45 to 75% of TPGS, about 1 to 10% of the crystallization inhibitor member, and no citric acid stabilizer. These compositions are especially well adapted for use with soft gel capsules, hereinafter described.

In this embodiment, PEG 400 is the preferred solubilizing component due to superior solubilization of the active drug compound in this excipient and the preferred soft gelatin capsule processing parameters provided by lowering the melting point range of the fill material compared to that obtained by other related potential solubilizers, e.g., PEG 1450, PEG 3550, PEG 4000, PEG 6000, etc.

The co-solubilizer/surfactant TPGS component and the crystallization inhibitor member component are as previously described. In this embodiment, copovidone (PVP-polyvinyl acetate) may be especially useful as the crystallization inhibitor member component.

As stated, there is no citric acid stabilizer in the composition according to this embodiment. However, the dosage forms may optionally include a pharmaceutically acceptable stabilizer of the active compound, including various inorganic acids (for example: hydrochloric acid, and the like) or other organic mono-, di-, or tri-carboxylic acids (for example: acetic acid, ascorbic acid, methanesulfonic acid, citric acid, succinic acid, tartaric acid, and the like) and various salts of said acids (for example sodium citrate, sodium succinate, sodium tartrate, and the like).

The formulations according to this embodiment may optionally also contain a pharmaceutically acceptable antioxidant for stabilization of the dosage form. Examples include ascorbic acid, BHA, BHT, propyl gallate, Vitamin E, and the like. The dosage forms may also contain glycerin and/or another suitable plasticizer for physical stability when encapsulated in a soft gelatin capsule.

In order to prepare the compositions according to the further embodiment hereinabove described, various preparation means available to the skilled artisan may be utilized. It is preferred that the active compound (2R)-2-[[(4-chlorophenyl)sulfonyl][[2-fluoro-4-(1,2,4-oxadiazol-3-yl)phenyl]methyl]amino]-5,5,5-trifluoropentanamide be dissolved at elevated temperature in an admixture solution of the polyethylene glycol (PEG), Vitamin E polyethylene glycol succinate, and crystallization inhibitor member using apparatus and procedures available in the art.

The compositions of the invention herein described according to the various embodiments may then be further adapted for oral administration in discrete units such as capsules. These capsules may be hard or soft. For instance, for oral administration in the form of a capsule, the compositions herein described containing the active drug component may be utilized as is, or can be further combined with an oral, non-toxic pharmaceutically acceptable inert carrier such as ethanol, glycerol, glycerin, water, and the like. The compositions of the invention may be encapsulated as liquid, semisolid or solid matrices. Powders may be prepared, for example, by comminuting the composition of the invention, or the active compound, to a suitable fine size and if desired, further mixing with a similarly comminuted pharmaceutical carrier such as an edible carbohydrate, as, for example, starch or mannitol.

Capsules are then made by filling fowled gelatin sheaths or shells. In addition to gelatin, other materials for the capsule sheath or shell include hydroxypropyl methylcellulose (HPMC), cellulose, methylcellulose, starch, other materials, and combinations of any of the foregoing.

Other methods for preparing capsules (both hard and soft) available to the skilled artisan may also be utilized. Flavoring, preservative, dispersing, and coloring agent can also be present, if desired. Glidants and lubricants such as colloidal silica, talc, magnesium stearate, calcium stearate, or solid polyethylene glycol can be added to the mixture before the filling operation. A disintegrating or solubilizing agent such as agar-agar, calcium carbonate, or sodium carbonate can also be added to improve the availability of the medicament when the capsule is ingested. Moreover, when desired or necessary, suitable additional binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like.

Two-piece capsules may be banded, e.g. with a gelatin-based solution for hard gelatin capsules, or an HPMC-based solution for HPMC capsules. By way of non-limiting example, pharmaceutical capsules containing about 5 mg., about 10 mg., about 20 mg. and about 50 mg., respectively, of the active compound (2R)-2-[[(4-chlorophenyl)sulfonyl][[2-fluoro-4-(1,2,4-oxadiazol-3-yl)phenyl]methyl]amino]-5,5,5-trifluoropentanamide may be made using the compositions herein described. Other dosage units are within the scope hereof.

In particular, capsules containing (2R)-2-[[(4-chlorophenyl)sulfonyl][[2-fluoro-4-(1,2,4-oxadiazol-3-yl)phenyl]methyl]amino]-5,5,5-trifluoropentanamide have demonstrated good in vitro dissolution rates, and also good oral bioavailability in dogs. Even more importantly, the compositions according to the various embodiments of the invention have demonstrated consistent and good bioavailability in humans when delivered orally using the capsule mechanism. This enhanced bioavailability is unexpected based on the presence of significant drug precipitation observed during in vitro studies (see Table V, hereinafter set forth), and a lack of in vitro-in vivo correlation.

The capsule compositions of the invention containing (2R)-2-[[(4-chlorophenyl)sulfonyl][[2-fluoro-4-(1,2,4-oxadiazol-3-yl)phenyl]methyl]amino]-5,5,5-trifluoropentanamide are highly storage stable, demonstrating good long-term chemical and physical stability. This means that they exhibit little (less than about 5%) degradation for at least about 12 months, and preferably for at least about 24 months, when stored in a closed container under either approximately 25° C./60% relative humidity, or at approximately 30° C./65% relative humidity as well.

In a further embodiment of the invention there is provided a method of treating or delaying the onset of Alzheimer's disease, cerebral amyloid angiopathy, mild cognitive impairment and/or Down syndrome, as well as the treatment of head trauma, traumatic brain injury, and/or dementia pugilistica, which comprises administering to a patient a therapeutically effective amount of a pharmaceutical capsule composition according to one or more of the embodiments hereinabove described. There is also provided a method of treating Alzheimer's disease in a patient, comprising administering to the patient a therapeutically effective amount of a pharmaceutical capsule composition according to one or more of the embodiments hereinabove described. Further provided is a method of inhibiting the functioning of a γ-secretase enzyme comprising contacting the γ-secretase enzyme with an effective amount of a pharmaceutical capsule composition according to one or more of the embodiments hereinabove described. Also provided is a method of inhibiting the production of β-amyloid peptide in a patient, comprising contacting a γ-secretase enzyme in the patient with an effective amount of a pharmaceutical capsule composition according to one or more of the embodiments hereinabove described. Further, a method of inhibiting the production of β-amyloid peptide in a patient comprises administering to the patient a therapeutically effective amount of a pharmaceutical capsule composition according to one or more of the embodiments hereinabove described. The term "therapeutically effective amount" means the total amount of the active component of the method that is sufficient to show a patient benefit, i.e., symptomatic or disease modifying treatment. When applied to an individual active ingredient, administered alone, the term refers to that ingredient alone. When applied to a combination, the term refers to combined amounts of the active ingredients that result in the therapeutic effect, whether administered in combination, serially or simultaneously.

EXAMPLES

The following examples illustrate various preferred aspects of the invention, but should not be construed as limiting the scope thereof.

Example 1

TABLE I

| Formulation #1: Hard Gelatin Capsule | | | | | |
|---|---|---|---|---|---|
| | | | Working Example | | |
| | | | Amounts (mg) | | |
| Ingredient | Function | Percent (w/w) | Size #2 Capsule | Size #1 Capsule | Size #0 Capsule |
| Active Compound | Active | 8.0% | 25.0 | 37.5 | 50.0 |
| Polyethylene Glycol 1450 | Solubilizer | 81.9% | 255.9375 | 383.906 | 511.875 |
| Vitamin E Polyethylene Glycol Succinate (TPGS) | Solubilizer and Surfactant for Precipitation Inhibition | 5.0% | 15.625 | 23.44 | 31.25 |
| Povidone (Polyvinylpyrrolidone) K12 | Crystallization Inhibitor | 5.0% | 15.625 | 23.44 | 31.25 |
| Citric Acid Anhydrous | pH Modifier for Stabilization | 0.1% | 0.3125 | 0.468 | 0.625 |
| Total | | 100.0% | 312.5 | 468.75 | 625.0 |

Manufacturing Process for Formulation #1 Hard Gelatin Capsule

1. Add PEG 1450 to batching vessel and mix at elevated temperature (e.g., 65° C.) to melt and give a solution.
2. Melt and transfer TPGS to batching vessel and mix at elevated temperature (e.g., 65° C.) to give a solution.
3. Add Citric Acid Anhydrous to batching vessel and mix at elevated temperature (e.g., 65° C.) to dissolve and give a solution.
4. Add Povidone (PVP) K12 to the batching vessel and mix at elevated temperature (e.g., 65° C.) to dissolve to give a solution.
5. Add active compound to the batching vessel and mix at elevated temperature (e.g., 65° C.) to dissolve and give a solution.
6. Fill appropriate amount of solution at elevated temperature (e.g., 65° C.) into capsules.
7. Band the capsules with gelatin.

Example 2

TABLE II

| Formulation #2: Hard Gelatin Capsule | | | | | |
|---|---|---|---|---|---|
| | | | Working Example | | |
| | | | Amounts (mg) | | |
| Ingredient | Function | Percent (w/w) | Size #2 Capsule | Size #1 Capsule | Size #0 Capsule |
| Active Compound | Active | 8.0% | 25.0 | 37.5 | 50.0 |
| Polyethylene Glycol 1450 | Solubilizer | 53.7% | 167.8125 | 251.72 | 335.625 |
| Vitamin E Polyethylene Glycol Succinate (TPGS) | Solubilizer and Surfactant for Precipitation Inhibition | 33.2% | 103.75 | 155.625 | 207.5 |

TABLE II-continued

| | | Formulation #2: Hard Gelatin Capsule | | | |
| | | | Working Example | | |
| | | | | Amounts (mg) | | |
| Ingredient | Function | Percent (w/w) | Size #2 Capsule | Size #1 Capsule | Size #0 Capsule |
| --- | --- | --- | --- | --- | --- |
| Copovidone (PVP VA64: Polyvinylpyrrolidone-Vinyl acetate) | Crystallization Inhibitor | 5.0% | 15.625 | 23.44 | 31.25 |
| Citric Acid Anhydrous | pH Modifier for Stabilization | 0.1% | 0.3125 | 0.468 | 0.625 |
| | Total | 100.0% | 312.5 | 468.75 | 625.0 |

Manufacturing Process for Formulation #2 Hard Gelatin Capsule
1. Add PEG 1450 to the batching vessel and mix at elevated temperature (e.g., 65° C.) to melt and give a solution.
2. Melt and transfer TPGS to the batching vessel and mix at elevated temperature (e.g., 65° C.) to give a solution.
3. Add Citric Acid Anhydrous to the batching vessel and mix at elevated temperature (e.g., 65° C.) to dissolve and give a solution.
4. Add Copovidone (PVP VA64) to the batching vessel and mix at elevated temperature (e.g., 65° C.) to dissolve to give a solution.
5. Add active compound to the batching vessel and mix at elevated temperature (e.g., 65° C.) to dissolve and give a solution,
6. Fill appropriate amount of solution at elevated temperature (e.g., 65° C.) into capsules.
7. Band the capsules with gelatin.

Manufacturing Process for Formulation #3 Soft Gelatin Capsule
1. Add PEG 400 and Copovidone (PVP VA64) to the batching vessel and mix at elevated temperature (e.g., 35-40° C.) to give a solution.
2. Melt and transfer TPGS to the batching vessel and mix at elevated temperature (e.g., 35-40° C.) to give a solution.
3. Add active compound to the batching vessel and mix at elevated temperature (e.g., 35-40° C.) to dissolve and give a solution.
6. Transfer the gelatin solution and formulation fill solution into the encapsulator and encapsulate an appropriate amount of formulation fill solution s at elevated temperature (e.g., 35-40° C.) into soft gelatin capsules.
7. Dry the capsules.
8. Perform a finish wash of the capsules.

Example 3

TABLE III

| | | Formulation #3: Soft Gelatin Capsule | | | |
| | | | Working Example | | |
| | | | | Amounts (mg) | | |
| Ingredient | Function | Percent (w/w) | Size #6 Capsule | Size #10 Capsule | Size #12 Capsule |
| --- | --- | --- | --- | --- | --- |
| Active Compound | Active | 15.0% | 50.0 | 75.0 | 100.0 |
| Polyethylene Glycol 400 | Solubilizer | 20.0% | 66.7 | 100.0 | 133.4 |
| Vitamin E Polyethylene Glycol Succinate (TPGS) | Solubilizer and Surfactant for Precipitation Inhibition | 60.0% | 200.1 | 300.0 | 400.2 |
| Copovidone (PVP VA64: Polyvinylpyrrolidone-Vinyl acetate) | Crystallization Inhibitor | 5.0% | 16.675 | 25.0 | 33.4 |
| | Total | 100.0% | 333.5 | 500.0 | 667.0 |

Example 4

TABLE IV

Formation of the Degradation Product in Solutions of Prototype Solubilized Capsule Formulations of the Active Compound

| Formulation | Percent Degradation Compound After 7 Days at 65° C. |
|---|---|
| 85.0% PEG 1450/5.0% TPGS/10.0% Active Compound | 0.14% |
| 85.0% PEG 1450/5.0% Polysorbate 80/10.0% Active Compound | 0.44% |
| 85.0% PEG 1450/5.0% PLURONIC® F127/10.0% Active Compound | 0.42% |

Example 5

TABLE V

Crash-Resistance Studies on Active Compound Solubilized Hard Gelatin Capsule Formulations

| Formulation | Percent of Theory (400 mcg/mL) Active Compound Dissolved | | |
|---|---|---|---|
| | 30 min. | 60 min. | 120 min. |
| 82.2% PEG 1450/5.0% TPGS/5% PVP K12/0.1% Citric Acid 7.7% ACTIVE COMPOUND Size #0 Hard Gelatin Capsule: 50 mg Strength | 10.8 | 2.7 | 2.2 |
| 87.2% TPGS/5.0% PVP K12/0.1% Citric Acid 7.7% ACTIVE COMPOUND Size #0 Hard Gelatin Capsule: 50 mg Strength | 39.1 | 42.8 | 40.4 |
| 54.0.% PEG 1450/33.2% TPGS/5% PVP K12/0.1% Citric Acid 7.7% ACTIVE COMPOUND Size #0 Hard Gelatin Capsule: 50 mg Strength | 47.7 | 21.8 | 14.2 |
| 87.2% TPGS/5.0% PVP VA64/0.1% Citric Acid 7.7% ACTIVE COMPOUND Size #0 Hard Gelatin Capsule: 50 mg Strength | 47.7 | 88.1 | 92.8 |
| 53.7.% PEG 1450/33.2% TPGS/5% PVP VA64/0.1% Citric Acid 8.0% ACTIVE COMPOUND Size #0 Hard Gelatin Capsule (HGC): 50 mg Strength | 77.6 | 86.8 | 20.4 |

Capsule placed in 125 mL pH 4.5 acetate buffer at 37° C. with stirring at 100-rpm.
Aliquots filtered at 30, 60 and 120 minutes.
Concentration of Active Compound quantified in each filtrate by HPLC.

Example 6

TABLE VI

Solubility of ACTIVE COMPOUND Solubilized Capsule Formulations in FaSSIF* at 37° C.

| Formulation | ACTIVE COMPOUND Concentration (µg/mL) | | | | |
|---|---|---|---|---|---|
| | 5 Min. | 15 Min. | 30 Min. | 60 Min. | 24 Hr. |
| ACTIVE COMPOUND Drug Substance | 2.5 | 3.8 | 4.6 | 6.0 | 7.7 |
| 8.0% ACTIVE COMPOUND in PEG 400 | 85.8 | 11.0 | 9.2 | 8.7 | 12.3 |
| 82.2% PEG 1450/5.0% TPGS/5.0% PVP K12/0.1% Citric Acid/ 7.7% ACTIVE COMPOUND Size #0 Hard Gelatin Capsule Formulation: 50 mg Strength | 122.9 | 148.8 | 13.2 | 12.4 | 14.0 |
| 87.2% TPGS/5.0% PVP K12/0.1% Citric Acid/ 7.7% ACTIVE COMPOUND Size #0 Hard Gelatin Capsule Formulation: 50 mg Strength | 292.7 | 471.4 | 349.4 | 313.9 | 228.6 |
| 54.0% PEG 1450/33.2% TPGS/5.0% PVP K12/0.1% Citric Acid/ 7.7% ACTIVE COMPOUND Size #0 Hard Gelatin Capsule Formulation: 50 mg Strength | 268.1 | 286.2 | 98.3 | 70.5 | 39.8 |
| 87.2% TPGS/5.0% PVP VA64/0.1% Citric Acid/ 7.7% ACTIVE COMPOUND Size #0 Hard Gelatin Capsule Formulation: 50 mg Strength | 347.7 | 555.2 | 634.3 | 650.3 | 211.4 |
| 60.0% TPGS/20.0% PEG 400/5.0% PVP K30/ 15.0% ACTIVE COMPOUND Soft Gelatin Capsule Formulation | 248.6 | 181.2 | 78.6 | 70.0 | 60.5 |
| 60.0% TPGS/20.0% PEG 400/5.0% PVP VA64/ 15.0% ACTIVE COMPOUND Soft Gelatin Capsule Formulation | 394.9 | 372.5 | 379.4 | 172.2 | 68.2 |

*Fasted State Simulated Intestinal Fluid: Sodium Taurocholate (3 mM)/Lecithin (0.75 mM)/Sodium Hydroxide (0.174 g)/Sodium Phosphate Monobasic (1.977 g)/Sodium Chloride (3.093 g)/Purified Water (qs to 500 mL): pH 6.5, osmolarity ~270 mOsmol/kg

Example 7

TABLE VII

Solubility of ACTIVE COMPOUND Solubilized Capsule Formulations in FeSSIF* at 37° C.

| Formulation | ACTIVE COMPOUND Concentration (µg/mL) | | | | |
|---|---|---|---|---|---|
| | 5 Min. | 15 Min. | 30 Min. | 60 Min. | 24 Hr. |
| ACTIVE COMPOUND Drug Substance | 9.7 | 11.5 | 13.3 | 15.3 | 22.4 |
| 8.0% ACTIVE COMPOUND in PEG 400 | 311.7 | 19.1 | 18.7 | 16.3 | 22.4 |
| 82.2% PEG 1450/5.0% TPGS/5.0% PVP K12/ 0.1% Citric Acid/ 7.7% ACTIVE COMPOUND Size #0 Hard Gelatin Capsule Formulation: 50 mg Strength | 5.6 | 23.9 | 19.9 | 20.9 | 24.1 |
| 87.2% TPGS/5.0% PVP K12/0.1% Citric Acid/ 7.7% ACTIVE COMPOUND Size #0 Hard Gelatin Capsule Formulation: 50 mg Strength | 378.1 | 485.9 | 214.0 | 187.1 | 151.0 |
| 54.0% PEG 1450/33.2% TPGS/5.0% PVP K12/ 0.1% Citric Acid/ 7.7% ACTIVE COMPOUND Size #0 Hard Gelatin Capsule Formulation: 50 mg Strength | 170.2 | 409.6 | 90.0 | 51.3 | 56.8 |
| 87.2% TPGS/5.0% PVP VA64/0.1% Citric Acid/ 7.7% ACTIVE COMPOUND Size #0 Hard Gelatin Capsule Formulation: 50 mg Strength | 247.6 | 530.3 | 601.4 | 620.8 | 135.0 |
| 60.0% TPGS/20.0% PEG 400/5.0% PVP K30/ 15.0% ACTIVE COMPOUND Soft Gelatin Capsule Formulation | 409.1 | 423.8 | 64.7 | 50.6 | 45.9 |
| 60.0% TPGS/20.0% PEG 400/5.0% PVP VA64/ 15.0% ACTIVE COMPOUND Soft Gelatin Capsule Formulation | 527.1 | 549.6 | 427.6 | 106.2 | 50.0 |

*Fed State Simulated Intestinal Fluid: Sodium Taurocholate (15 mM)/Lecithin (3.75 mM)/Sodium Hydroxide (4.04 g)/Glacial Acetic Acid (8.65 g)/Sodium Chloride (11.874 g)/Purified Water (qs to 1000 mL): pH 5.0, osmolarity ~670 mOsmol/kg.

Example 8

TABLE VIII

Solubility of ACTIVE COMPOUND Solubilized Capsule Formulations in SGF* at 37° C.

| Formulation | ACTIVE COMPOUND Concentration (µg/mL) | | | | |
|---|---|---|---|---|---|
| | 5 Min. | 15 Min. | 30 Min. | 60 Min. | 24 Hr. |
| ACTIVE COMPOUND Drug Substance | 0.0 | 4.6 | 1.6 | 1.0 | 1.0 |
| 8.0% ACTIVE COMPOUND in PEG 400 | 13.7 | 11.4 | 14.2 | 2.3 | 1.1 |
| 82.2% PEG 1450/5.0% TPGS/5.0% PVP K12/ 0.1% Citric Acid/ 7.7% ACTIVE COMPOUND Size #0 Hard Gelatin Capsule Formulation: 50 mg Strength | 98.5 | 127.0 | 17.3 | 14.0 | 19.1 |
| 87.2% TPGS/5.0% PVP K12/0.1% Citric Acid/ 7.7% ACTIVE COMPOUND Size #0 Hard Gelatin Capsule Formulation: 50 mg Strength | 273.4 | 484.9 | 453.8 | 295.5 | 253.8 |
| 54.0% PEG 1450/33.2% TPGS/5.0% PVP K12/ 0.1% Citric Acid/ 7.7% ACTIVE COMPOUND Size #0 Hard Gelatin Capsule Formulation: 50 mg Strength | 69.9 | 190.5 | 231.5 | 122.5 | 100.7 |
| 87.2% TPGS/5.0% PVP VA64/0.1% Citric Acid/ 7.7% ACTIVE COMPOUND Size #0 Hard Gelatin Capsule Formulation: 50 mg Strength | 267.8 | 522.2 | 680.4 | 699.6 | 612.7 |

TABLE VIII-continued

Solubility of ACTIVE COMPOUND Solubilized Capsule Formulations in SGF* at 37° C.

| Formulation | ACTIVE COMPOUND Concentration (μg/mL) | | | | |
|---|---|---|---|---|---|
| | 5 Min. | 15 Min. | 30 Min. | 60 Min. | 24 Hr. |
| 60.0% TPGS/20.0% PEG 400/5.0% PVP K30/ 15.0% ACTIVE COMPOUND Soft Gel Capsule Formulation | 106.0 | 183.2 | 96.6 | 67.2 | 91.7 |
| 60.0% TPGS/20.0% PEG 400/5.0% PVP VA64/ 15.0% ACTIVE COMPOUND Soft Gelatin Capsule Formulation | 263.6 | 321.7 | 348.3 | 401.8 | 133.0 |

*Simulated Gastric Fluid: Sodium Chloride (2.0 g)/Purified Pepsin (3.2 g, activity of 800 to 2500 units per mg of protein)/Hydrochloric Acid (7.0)/Purified Water (qs to 1000 mL)

Example 9

TABLE IX

Bioavailability of ACTIVE COMPOUND Solubilized Capsule Formulations in Dogs

| Formulation | Absolute Bioavailability |
|---|---|
| Micronized Suspension | 5% |
| Nanosuspension | 10% |
| 82.2% PEG 1450/5.0% TPGS/5.0% PVP K12/0.1% Citric Acid/ 7.7% ACTIVE COMPOUND Size #0 Hard Gelatin Capsule Formulation: 50 mg Strength | ~45-60% |
| 87.2% TPGS/5.0% PVP K12/0.1% Citric Acid/ 7.7% ACTIVE COMPOUND Size #0 Hard Gelatin Capsule Formulation: 50 mg Strength | ~45-60% |
| 54.0% PEG 1450/33.2% TPGS/5.0% PVP K12/0.1% Citric Acid/ 7.7% ACTIVE COMPOUND Size #0 Hard Gelatin Capsule Formulation: 50 mg Strength | ~45-60% |
| 87.2% TPGS/5.0% PVP VA64/0.1% Citric Acid/ 7.7% ACTIVE COMPOUND Size #0 Hard Gelatin Capsule Formulation: 50 mg Strength | ~45-60% |
| 60.0% TPGS/20.0% PEG 400/5.0% PVP VA64/ 15.0% ACTIVE COMPOUND Soft Gelatin Capsule Formulation: 75 mg Strength | ~45-60% |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A pharmaceutical composition comprising about 0.1 to 20% of (2R)-2-[[(4-chlorophenyl)sulfonyl][[2-fluoro-4-(1,2,4-oxadiazol-3-yl)phenyl]methyl]amino]-5,5,5-trifluoropentanamide, up to about 90% of polyethylene glycol (PEG), up to about 90% of Vitamin E polyethylene glycol succinate (TPGS), about 0.1 to 20% of a crystallization inhibitor member selected from the group consisting of polyvinylpryrrolidone (PVP) and copovidone (PVP-Polyvinyl acetate); and about 0.05 to 5% of citric acid.

2. The pharmaceutical composition of claim 1, comprising about 0.1 to 20% of (2R)-2-[[(4-chlorophenyl)sulfonyl][[2-fluoro-4-(1,2,4-oxadiazol-3-yl)phenyl]methyl]amino]-5,5,5-trifluoropentanamide, about 35 to 90% of PEG, about 2 to 90% of TPGS, about 0.1 to 20% of said crystallization inhibitor member; and about 0.05 to 1% of citric acid.

3. The pharmaceutical composition of claim 2, comprising about 0.1 to 10% of (2R)-2-[[(4-chlorophenyl)sulfonyl][[2-fluoro-4-(1,2,4-oxadiazol-3-yl)phenyl]methyl]amino]-5,5,5-trifluoropentanamide, about 50 to 85% of PEG, about 5 to 40% of TPGS, about 1 to 10% of said crystallization inhibitor member; and about 0.05 to 1% of citric acid.

4. The pharmaceutical composition of claim 3, comprising about 8% of (2R)-2-[[(4-chlorophenyl)sulfonyl][[2-fluoro-4-(1,2,4-oxadiazol-3-yl)phenyl]methyl]amino]-5,5,5-trifluoropentanamide, about 81.9% of PEG, about 5% of TPGS, about 5% of said crystallization inhibitor member; and about 0.1% of citric acid.

5. The pharmaceutical composition of claim 3, comprising about 8% of (2R)-2-[[(4-chlorophenyl) sulfonyl][[2-fluoro-4-(1,2,4-oxadiazol-3-yl)phenyl]methyl]amino]-5,5,5-trifluoropentanamide, about 53.7% of PEG, about 33.2% of TPGS, about 5% of said crystallization inhibitor member; and about 0.1% of citric acid.

6. The pharmaceutical composition of claim 3, wherein said PEG is PEG 1450.

7. The pharmaceutical composition of claim 4, wherein said crystallization inhibitor member is PVP.

8. The pharmaceutical composition of claim 5, wherein said crystallization inhibitor member is copovidone.

9. A pharmaceutical capsule containing the composition of claim 3.

10. The pharmaceutical capsule of claim 9, wherein said capsule is comprised of gelatin.

11. The pharmaceutical capsule of claim 10, wherein said capsule is a hard gelatin capsule.

12. The pharmaceutical composition of claim 1, wherein said (2R)-2-[[(4-chlorophenyl)sulfonyl][[2-fluoro-4-(1,2,4-oxadiazol-3-yl)phenyl]methyl]amino]-5,5,5-trifluoropentanamide is solubilized in said PEG, said TPGS, said crystallization inhibitor member and said citric acid.

13. A pharmaceutical composition comprising about 0.1 to 25% of (2R)-2-[[(4-chlorophenyl)sulfonyl][[2-fluoro-4-(1,2,4-oxadiazol-3-yl)phenyl]methyl]amino]-5,5,5-trifluoropentanamide, up to about 90% of polyethylene glycol (PEG), up to about 90% of Vitamin E polyethylene glycol succinate (TPGS), and about 0.1 to 20% of a crystallization inhibitor member selected from the group consisting of polyvinylpryrrolidone (PVP) and copovidone (PVP-Polyvinyl acetate); wherein said composition does not contain citric acid.

14. The pharmaceutical composition of claim 13, comprising about 0.1 to 20% of (2R)-2-[[(4-chlorophenyl)sulfonyl][[2-fluoro-4-(1,2,4-oxadiazol-3-yl)phenyl]methyl]amino]-5,5,5-trifluoropentanamide, about 5 to 75% of PEG, about 5 to 75% of TPGS, and about 0.1 to 20% of said crystallization inhibitor member.

15. The pharmaceutical composition of claim 14, comprising about 0.5 to 20% of (2R)-2-[[(4-chlorophenyl)sulfonyl][[2-fluoro-4-(1,2,4-oxadiazol-3-yl)phenyl]methyl]amino]-5,5,5-trifluoropentanamide, about 10 to 30% of PEG, about 45 to 75% of TPGS, and about 1 to 10% of said crystallization inhibitor member.

16. The pharmaceutical composition of claim 15, comprising about 15% of (2R)-2-[[(4-chlorophenyl)sulfonyl][[2-fluoro-4-(1,2,4-oxadiazol-3-yl)phenyl]methyl]amino]-5,5,5-trifluoropentananiide, about 20% of PEG, about 60% of TPGS, and about 5% of said crystallization inhibitor member.

17. The pharmaceutical composition of claim 15, wherein said crystallization inhibitor member is copovidone.

18. The pharmaceutical composition of claim 16, wherein said crystallization inhibitor member is copovidone.

19. The pharmaceutical composition of claim 15, wherein said PEG is PEG 400.

20. The pharmaceutical composition of claim 16, wherein said PEG is PEG 400.

21. A pharmaceutical capsule containing the composition of claim 15.

22. The pharmaceutical capsule of claim 21, wherein said capsule is comprised of gelatin.

23. The pharmaceutical capsule of claim 22, wherein said capsule is a soft gelatin capsule.

24. The capsule of claim 23, wherein said capsule and said composition are storage stable for at least about 12 months.

25. The capsule of claim 24, wherein said capsule and said composition are storage stable for at least about 12 months.

26. The capsule of claim 11, wherein said capsule and said composition are storage stable for at least about 12 months.

27. The capsule of claim 26, wherein said capsule and said composition are storage stable for at least about 24 months.

28. A method of making a pharmaceutical composition which comprises dissolving (2R)-2-[[(4-chlorophenyl)sulfonyl][[2-fluoro-4-(1,2,4-oxadiazol-3-yl)phenyl]methyl]amino]-5,5,5-trifluoropentanamide in a mixture of PEG, TPGS, and one crystallization inhibitor member selected from the group consisting of PVP and copovidone.

29. The method of claim 28, further comprising the step of adding said composition to a pharmaceutical capsule.

30. A method of treating or delaying the onset of Alzheimer's disease, cerebral amyloid angiopathy, mild cognitive impairment and/or Down syndrome, as well as the treatment of head trauma, traumatic brain injury, and/or dementia pugilistica, which comprises administering to a patient a therapeutically effective amount of a pharmaceutical capsule containing the composition of claim 1 or claim 13.

* * * * *

UNITED STATES PATENT AND TRADEMARK OFFICE
CERTIFICATE OF CORRECTION

PATENT NO.           : 8,252,821 B2                                              Page 1 of 1
APPLICATION NO.      : 12/758385
DATED                : August 28, 2012
INVENTOR(S)          : Sachin Chandran et al.

It is certified that error appears in the above-identified patent and that said Letters Patent is hereby corrected as shown below:

On the Title Page:

Item (57), ABSTRACT:

Column 2, line 5 (Abstract), change "polyvinylpryrrolidone" to -- polyvinylpyrrolidone --.

In the Specification:

Column 4, line 14, change "polyvinylpryrrolidone" to -- polyvinylpyrrolidone --.

Column 4, line 33, change "polyvinylpryrrolidone" to -- polyvinylpyrrolidone --.

Column 5, lines 27 and 28, change "polyvinylpryrrolidone" to -- polyvinylpyrrolidone --.

Column 6, line 5, change "polyvinylpryrrolidone" to -- polyvinylpyrrolidone --.

Column 6, lines 62 and 63, change "polyvinylpryrrolidone" to -- polyvinylpyrrolidone --.

In the Claims:

Claim 1:

Column 17, lines 61 and 62, change "polyvinylpryrrolidone" to -- polyvinylpyrrolidone --.

Claim 13:

Column 18, lines 59 and 60, change "polyvinylpryrrolidone" to -- polyvinylpyrrolidone --.

Claim 16:

Column 19, line 10, change "trifluoropentananiide," and insert -- trifluoropentanamide, --.

Signed and Sealed this
Eighth Day of April, 2014

Michelle K. Lee
*Deputy Director of the United States Patent and Trademark Office*